US010265098B2

(12) United States Patent
Asleson et al.

(10) Patent No.: US 10,265,098 B2
(45) Date of Patent: Apr. 23, 2019

(54) MULTI-PURPOSE MEDICAL TOOLS AND METHODS FOR GAINING ACCESS TO EXTRAVASCULAR SPACES IN A PATIENT

(71) Applicant: Medtronic, Inc., Minneapolis, MN (US)

(72) Inventors: Andrea J. Asleson, Maple Grove, MN (US); Ronald A. Drake, St. Louis Park, MN (US); Trent M. Fischer, St. Paul, MN (US); Lester O. Stener, Hudson, WI (US); Bridget A. Portway, White Bear Township, MN (US)

(73) Assignee: Medtronic, Inc., Minneapolis, MN (US)

( * ) Notice: Subject to any disclaimer, the term of this patent is extended or adjusted under 35 U.S.C. 154(b) by 339 days.

(21) Appl. No.: 15/139,686

(22) Filed: Apr. 27, 2016

(65) Prior Publication Data

US 2017/0119434 A1 May 4, 2017

Related U.S. Application Data

(60) Provisional application No. 62/247,889, filed on Oct. 29, 2015.

(51) Int. Cl.
| | |
|---|---|
| *A61B 19/00* | (2006.01) |
| *A61N 1/05* | (2006.01) |
| *A61B 17/34* | (2006.01) |
| *A61B 17/00* | (2006.01) |
| *A61N 1/372* | (2006.01) |
| *A61B 17/16* | (2006.01) |

(52) U.S. Cl.
CPC .......... *A61B 17/3468* (2013.01); *A61B 17/00* (2013.01); *A61B 17/1691* (2013.01); *A61N 1/372* (2013.01); *A61N 1/05* (2013.01)

(58) Field of Classification Search
CPC ...... A61B 17/3468; A61B 17/00; A61N 1/05; A61N 1/372
See application file for complete search history.

(56) References Cited

U.S. PATENT DOCUMENTS

| | | | |
|---|---|---|---|
| 4,687,471 A | 8/1987 | Twardowski et al. | |
| 8,574,192 B2 | 11/2013 | Haarala et al. | |
| 2004/0143284 A1* | 7/2004 | Chin .................. | A61B 17/3468 606/192 |

(Continued)

FOREIGN PATENT DOCUMENTS

EP    2204127 A1    7/2010

OTHER PUBLICATIONS

Medtronic, Inc. 6996T Tunneling Tool, Technical Manual, 12 pages.
(Continued)

*Primary Examiner* — Tuan V Nguyen

(57) ABSTRACT

This disclosure describes various examples of multi-purpose tools and associated methods for safely gaining access to extravascular spaces. The multi-purpose tools described herein are particularly suited for safely gaining access to the sub-sternal space underneath the sternum/ribcage as well as tunneling subcutaneously above the ribcage for the purpose of positioning of a medical electrical lead. This eliminates the need for separate tools for tunneling in different extravascular spaces by providing a single tool capable of the multiple uses.

15 Claims, 13 Drawing Sheets

(56) References Cited

U.S. PATENT DOCUMENTS

| | | |
|---|---|---|
| 2006/0015130 A1 | 1/2006 | Voorhees, Jr. et al. |
| 2012/0083794 A1 | 4/2012 | Martin et al. |
| 2014/0330248 A1 | 11/2014 | Thompson-Nauman et al. |
| 2015/0105793 A1 | 4/2015 | Cole |
| 2015/0133952 A1 | 5/2015 | Seifert et al. |
| 2015/0133953 A1 | 5/2015 | Seifert et al. |
| 2015/0209077 A1 | 7/2015 | Marshall |
| 2015/0306375 A1 | 10/2015 | Marshall et al. |
| 2015/0306410 A1 | 10/2015 | Marshall et al. |
| 2016/0158567 A1 | 6/2016 | Marshall et al. |

OTHER PUBLICATIONS

Spine Surgical Innovation Catalog, 2011; 52 pages.
(PCT/US2016/049376) PCT Notification of Transmittal of the International Search Report and the Written Opinion of the International Searching Authority, dated Nov. 21, 2016, 11 pages.

* cited by examiner

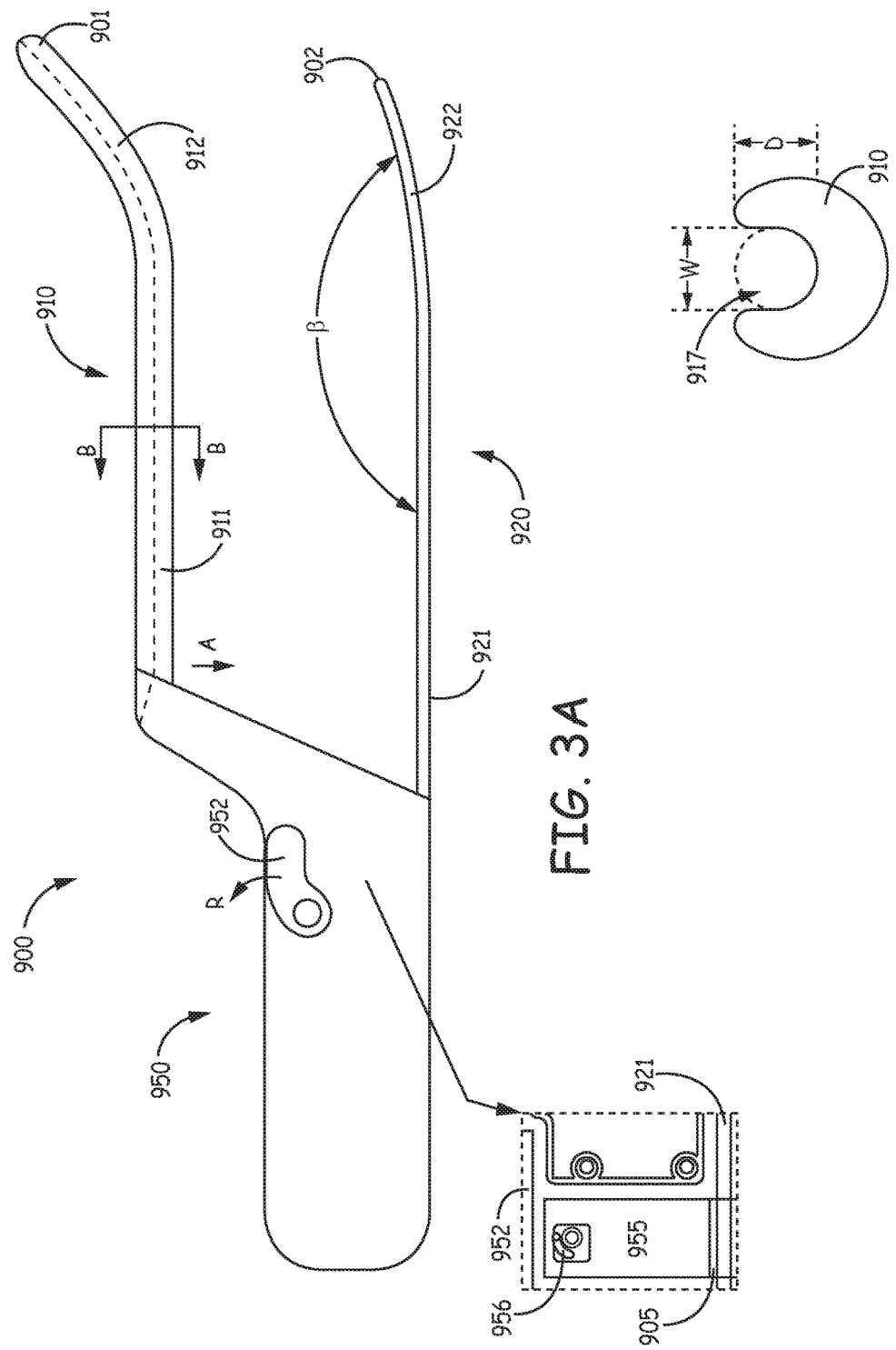

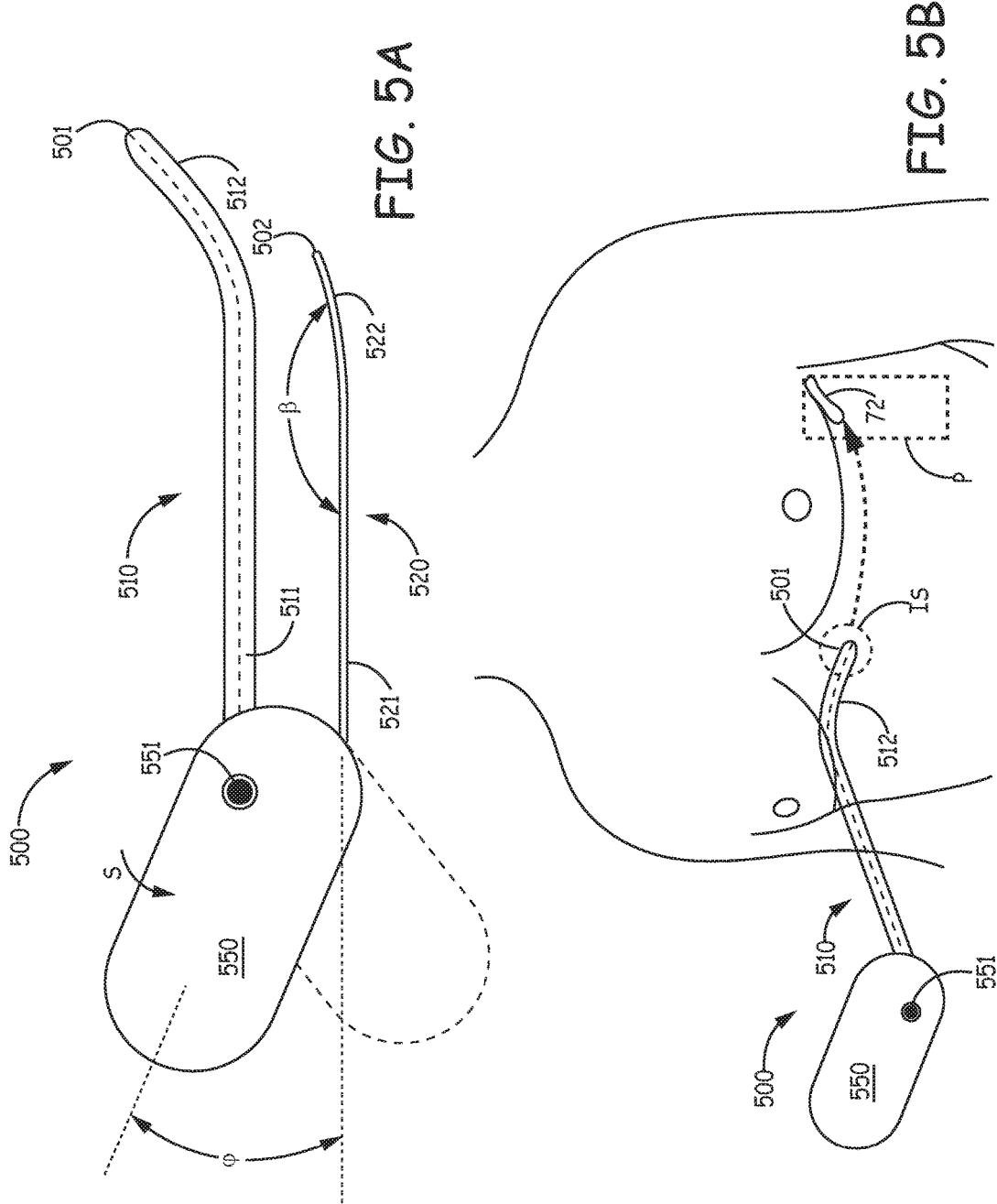

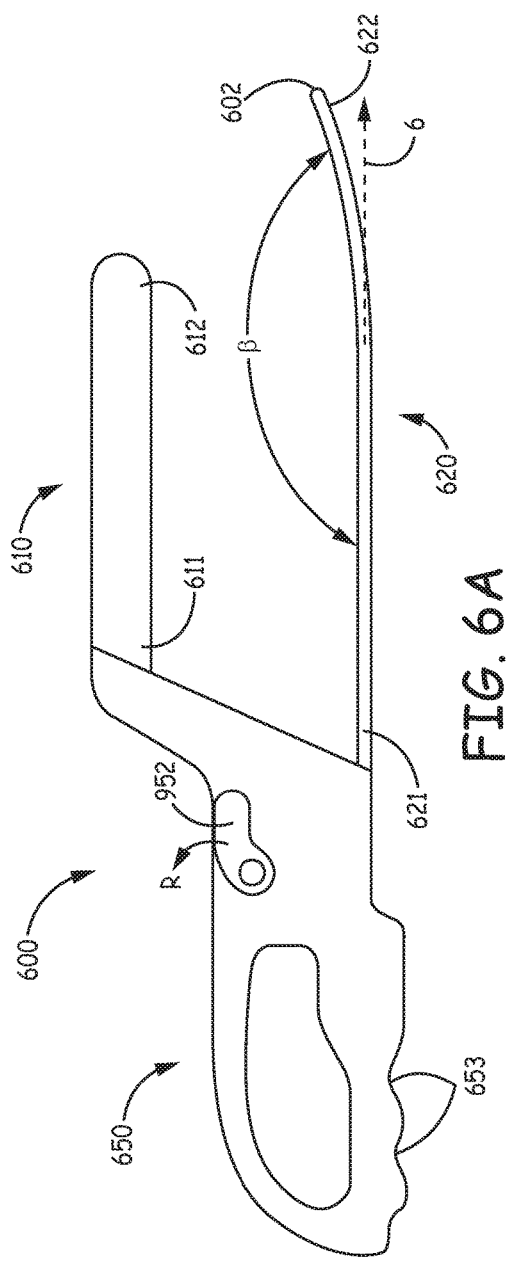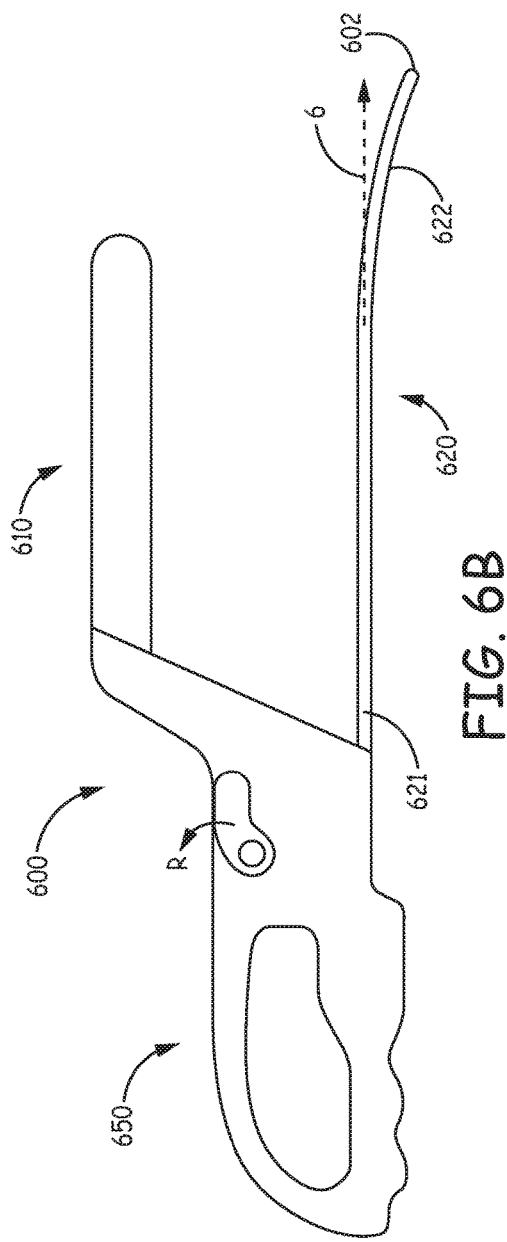

MULTI-PURPOSE MEDICAL TOOLS AND METHODS FOR GAINING ACCESS TO EXTRAVASCULAR SPACES IN A PATIENT

TECHNICAL FIELD

The present disclosure pertains to multi-purpose tools and associated methods for safely gaining access to extravascular spaces, and more particularly to those suited to safely gain access to at least two such spaces in a patient for the purpose of positioning of a medical electrical lead therein.

BACKGROUND

Implantable medical electrical leads, included in systems that are known in the art for delivering cardiac therapy and/or for providing cardiac monitoring, are often implanted transvenously within a heart of a patient. But extravascular implant sites may be preferred, for example, in those patients where vascular access is difficult, or because transvenous leads can become fibrosed in the heart over time, which makes lead revision and extraction procedures challenging.

SUMMARY

This disclosure describes various examples of multi-purpose tools and associated methods for safely gaining access to extravascular spaces. The multi-purpose tools described herein are particularly suited for safely gaining access to the sub-sternal space underneath the sternum/ribcage as well as tunneling subcutaneously above the ribcage for the purpose of positioning of a medical electrical lead.

In one example, this disclosure is directed to a multi-purpose tunneling tool comprising an elongate tunneling member, a handle, and an alignment horn. The elongate tunneling member includes a relatively straight proximal segment, a distal segment, and a blunt tip. The proximal segment of the elongate tunneling member defines a longitudinal axis of the tunneling member. The distal segment of the elongate tunneling member extends along a single pre-formed bend from the proximal segment to the blunt tip. The distal segment elongate tunneling member is co-planar with the proximal segment and the segments enclose an angle of between approximately 150 degrees and approximately 170 degrees. The handle includes a lock-and-release mechanism that forms a junction between the handle and the proximal segment of the tunneling member. The alignment horn extends from a first end thereof to a second end thereof, alongside and coplanar with the tunneling member. The alignment horn is relatively straight between the first and second ends thereof and substantially parallel to the tunneling member proximal segment. The first end of the alignment horn is coupled to the handle. The lock-and-release mechanism of the handle is configured to allow detachment of the handle from the tunneling member, and to allow rotation of the tunneling member 180 degrees about the longitudinal axis thereof, relative to the handle, from a first position to a second position, the tunneling member distal segment extending directly toward the alignment horn in the first position, and the tunneling member distal segment extending directly away from the alignment horn in the second position.

In another example, this disclosure provides a multi-purpose tunneling tool comprising an elongate tunneling member, a handle, and an alignment horn. The elongate tunneling member includes a relatively straight proximal segment, a distal segment, and a blunt tip, the proximal segment defining a longitudinal axis of the tunneling member, the distal segment extending along a single pre-formed bend from the proximal segment to the blunt tip, the distal segment being co-planar with the proximal segment, and the segments enclosing an angle of between approximately 150 degrees and approximately 170 degrees. The handle is joined to the proximal segment of the tunneling member. The alignment horn includes a first end, a second end, and a blunt tip terminating the second end, the horn extending from the first end to the second end alongside and coplanar with the tunneling member, and the horn being relatively straight between the first and second ends thereof and parallel to the proximal segment of the tunneling member, the first end of the alignment horn being coupled to the handle, the second end of the alignment horn extending along a single pre-formed bend, such that the blunt tip of the horn is directed away from the tunneling member, the second end being co-planar with a relatively straight remainder of the horn, and the second end and remainder enclosing an angle of between 150 degrees and 170 degrees.

In a further example, this disclosure provides a method for employing a tunneling tool. The method includes creating a sub-sternal tunnel in a patient by advancing an elongate tunneling member of the tool beneath a sternum of the patient, after having inserted a blunt tip of the tunneling member through an incision site of the patient, the advancing being guided by an alignment horn of the tool, the tunneling member further including a relatively straight proximal segment, and a distal segment extending along a single pre-formed bend from the proximal segment to the blunt tip, the distal segment being co-planar with the proximal segment, and the alignment horn extending from a first end thereof to a second end thereof, alongside and coplanar with the tunneling member, the horn being relatively straight between the first and second ends thereof and parallel to the proximal segment of the tunneling member. The method also includes removing the tunneling member of the tool from the sub-sternal tunnel and positioning a distal portion of a medical electrical lead within the sub-sternal tunnel, after removing the tunneling member. The method further includes creating a subcutaneous tunnel superficial to a rib cage of the patient, after creating the sub-sternal tunnel and removing the tunneling member of the tool therefrom, by inserting a blunt tip of the alignment horn of the tool through the incision site and then advancing the alignment horn subcutaneously around the rib cage to a subcutaneous pocket of the patient, the blunt tip of the alignment horn terminating the second end of the horn, and the second end of the horn extending along a single pre-formed bend, such that the blunt tip of the horn is directed away from the tunneling member, the second end being co-planar with a relatively straight remainder of the horn and positioning a proximal portion of the medical electrical lead within the subcutaneous tunnel, so that a connector terminal of the lead extends into the subcutaneous pocket.

In another example, the disclosure provides a method for employing a tunneling tool to create a subcutaneous tunnel within a patient, and to position a proximal portion of a medical electrical lead within the subcutaneous tunnel, after creating a sub-sternal tunnel in the patient with the tunneling tool. The method comprises rotating an elongate tunneling member of the tool 180 degrees relative to a handle of the tool so that a blunt tip of the tunneling member is directed away from an alignment horn of the tool, the tunneling member further including a relatively straight proximal segment joined to the handle and a distal segment extending along a pre-formed bend from the proximal segment to the blunt tip, the distal segment being coplanar with the with the proximal segment, and the alignment horn extending from a first end thereof to a second end thereof, alongside and coplanar with the proximal segment of the tunneling member, the horn being relatively straight between the first and second ends thereof and parallel to the proximal segment of the tunneling member; advancing the rotated tunneling member subcutaneously around a rib cage of the patient until the blunt tip reaches a subcutaneous pocket of the patient; detaching the handle from the proximal segment of the advanced tunneling member, the handle including a lock-and-release mechanism joining the proximal segment of the tunneling member thereto; attaching a connector terminal of the proximal portion of the medical electrical lead to the proximal segment of the advanced tunneling member, after detaching the handle; and applying a pull force to the distal segment of the advanced tunneling member, after attaching the connector terminal of the lead proximal portion to the proximal segment thereof, to bring the connector terminal through the subcutaneous tunnel and into the subcutaneous pocket.

This summary is intended to provide an overview of the subject matter described in this disclosure. It is not intended to provide an exclusive or exhaustive explanation of the apparatus and methods described in detail within the accompanying drawings and description below. Further details of one or more examples are set forth in the accompanying drawings and the description below.

BRIEF DESCRIPTION OF THE DRAWINGS

FIGS. 3A-3C are schematics illustrating various views of an example multi-purpose tool for creating both a sub-sternal tunnel and a subcutaneous tunnel in a patient.

FIG. 5A-B are schematics of various plan views of another example multi-purpose tool for creating both a sub-sternal tunnel and a subcutaneous tunnel in a patient.

FIGS. 6A-B are schematics of various plan views of another example multi-purpose tool.

DETAILED DESCRIPTION

The following detailed description is exemplary in nature and is not intended to limit, in any way, the scope, applicability, or configuration of the tools and techniques described in this disclosure. Rather, the following description provides practical examples, and those skilled in the art will recognize that some of the examples may have suitable alternatives.

Figure 1A:
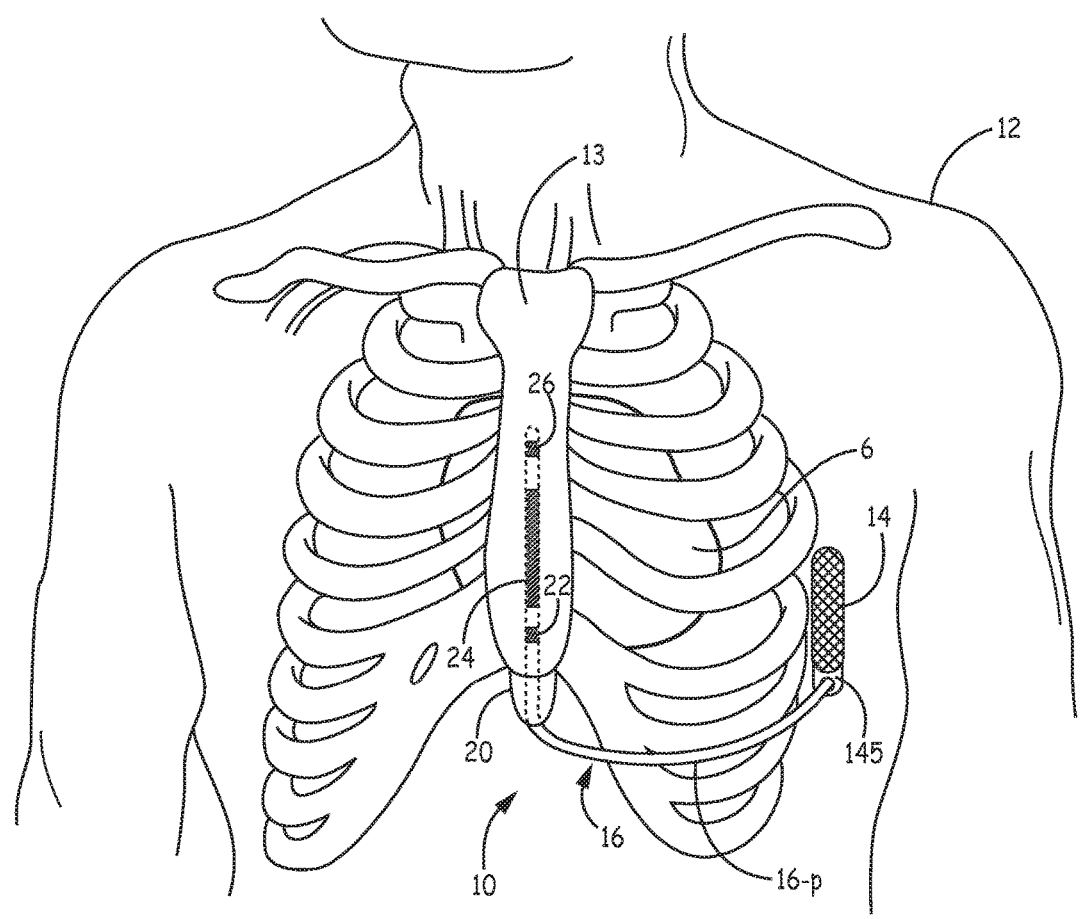
FIGS. 1A-B are schematics showing an exemplary extravascular implant of an exemplary extravascular medical system that includes an implantable pulse generator and an implantable medical electrical lead coupled thereto.
Figure 1B:
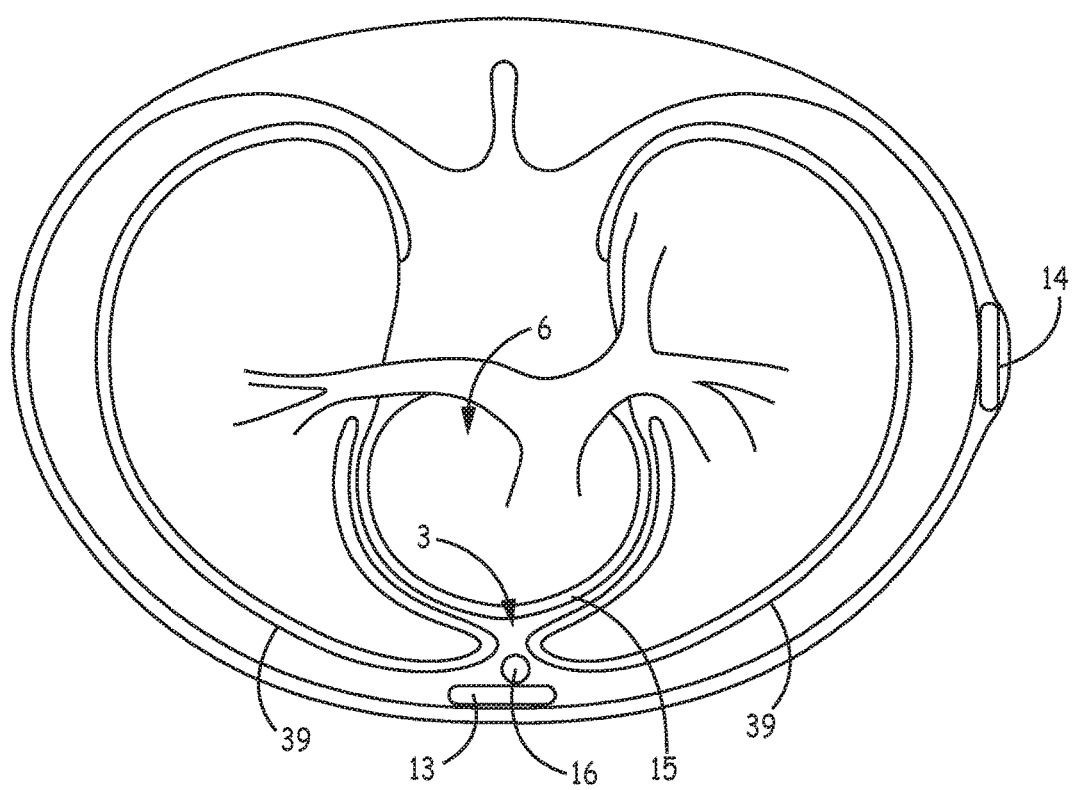

FIGS. 1A-B are schematics showing an exemplary extravascular implant of an exemplary extravascular medical system 10 that includes an implantable pulse generator 14 and an implantable medical electrical lead 16 coupled thereto. Pulse generator 14 is shown implanted in a subcutaneous space, or pocket formed on the left mid-axillary line of a patient 12, superficial to the patient's ribcage. Pulse generator 14, which may be configured to provide cardiac pacing and/or defibrillation therapy, includes a hermetically sealed housing in which the appropriate electronics and a power supply are contained, and which is formed from a conductive material, such as titanium, or from a combination of conductive and non-conductive materials. Pulse generator 14 further includes a connector module 145 by which lead 16 is electrically coupled to the electronics contained therein, for example, by electrical contacts contained within connector module 145 and a corresponding hermetically sealed feedthrough assembly, such as is known in the art. The conductive material of the pulse generator housing may be employed as an electrode, for example, to provide the aforementioned therapy in conjunction with one or more pace/sense electrodes 22, 26 and/or a defibrillation electrode 24 of lead 16. A proximal portion 16-$p$ of lead 16 is shown extending medially from pulse generator 14 toward a sternum 13 of the patient, for example, within a subcutaneous or submuscular tunnel above the ribcage, and a distal portion of lead 16 is shown extending in a superior direction adjacent to the sternum 13, for example within a tunnel formed in a sub-sternal space 3 (e.g., the loose connective tissue and/or sub-sternal musculature of the anterior mediastinum), wherein lead 16 bends in proximity to a xiphoid process 20 of sternum 13, to extend from the subcutaneous tunnel to the sub-sternal tunnel. With reference to FIG. 1B, sub-sternal space 3 may be generally viewed as being bounded laterally by pleurae 39 that enclose the patient's lungs, posteriorly by the pericardial sac 15 that encloses the patient's heart 6, and anteriorly by the sternum 13. In some instances, the anterior wall of the anterior mediastinum may also be formed by the transversus thoracis muscles and one or more costal cartilages.

Figure 2:
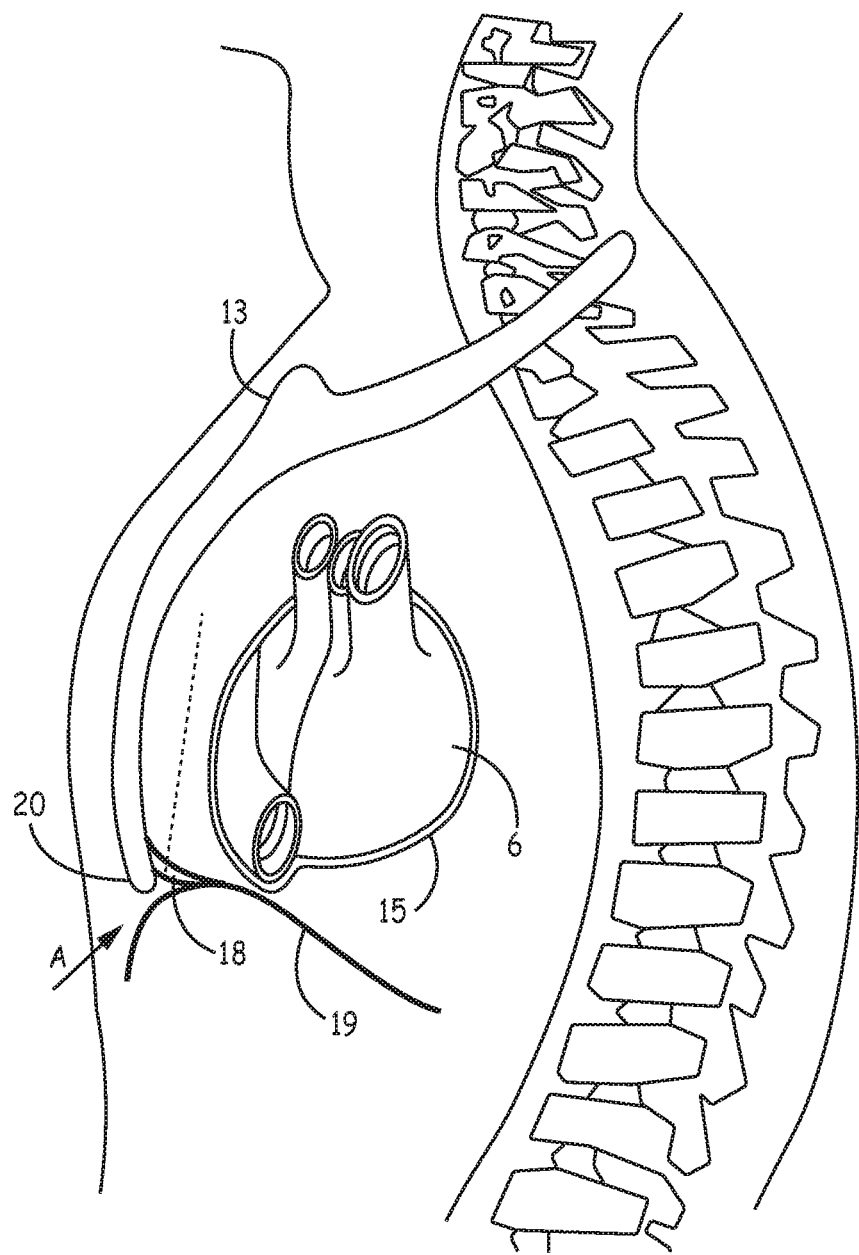
FIG. 2 is a schematic showing an access site for making a passageway between a patient's diaphragm and xiphoid process of sternum to create a sub-sternal tunnel in which to position the distal portion of a medical electrical lead.

FIG. 2 is a schematic showing an access site A for making a passageway between a patient's diaphragm 19 and xiphoid process 20 of sternum 13, for example, to create the aforementioned sub-sternal tunnel in which to position the distal portion of medical electrical lead 16. After making a superficial incision, an operator, using tools and techniques known to those skilled in the art, may open a passageway between diaphragmatic attachments 18 and diaphragm 19, for example, by blunt dissection, in which the operator may employ a tunneling tool, for example, the Medtronic® Model 6996T, to both create the passageway and then form a sub-sternal tunnel (e.g. along the dotted line of FIG. 2). However, because the boney structure of the sternum inhibits external palpation, the operator must take extra care, during the blunt dissection and/or tunneling, not to injure sub-sternal structures or the chest cavity, which could compromise the pleura 39 of the lungs or the heart 6. Thus, tools disclosed herein, for the purpose of passing a medical electrical lead into sub-sternal and subcutaneous regions (e.g., as shown in FIG. 1), help an operator to gaining access and/or form both a sub-sternal tunnel, for example, in a more controlled fashion that mitigates the risk of injuring bodily organs, and a subcutaneous tunnel.

FIG. 3A is a plan view of a multi-purpose tool 900 for creating both a sub-sternal tunnel and a subcutaneous tunnel in a patient, according to some embodiments. FIG. 3A illustrates tool 900 including a handle 950, an elongate tunneling member 920, which has a proximal segment 921 joined to handle 950, and an alignment horn 910, which has a first end 911 coupled to handle 950, and which extends, alongside and coplanar with tunneling member 920, from first end 911 to a second end 912 of horn 910, being relatively straight therebetween, and parallel to tunneling member proximal segment 921. FIG. 3A further illustrates each of tunneling member 920 and alignment horn 910 including a blunt tip 902, 901, wherein a distal segment 922 of tunneling member 920 extends along a single pre-formed bend from proximal segment 921 to blunt tip 902, such that blunt tip 902 is directed toward alignment horn 910, and such that tunneling member proximal segment 921 and distal segment 922 are coplanar and enclose an angle β. In one example, that angle β may be between approximately 150 degrees and approximately 170 degrees. However, the angle β may, in other examples, be greater than 170 degrees (but less than 180 degrees) and less than 150 degrees (but greater than 90 degrees). Similarly, second end 912 of alignment horn 910 is shown extending along a single pre-formed bend and being terminated by blunt tip 901; second end 912 of alignment horn 910 is coplanar with the relatively straight remainder of horn 910. Thus, alignment horn 910 may, similar to tunneling member 920, include a relatively straight first (or proximal) segment and a curved second (or distal) segment that extends along a single pre-formed bend from the straight first segment to blunt tip 901, such that blunt tip 901 is directed away from tunneling member 920. An angle enclosed by second end 912 and the straight remainder of alignment horn 910 may be similar to angle β of tunneling member 920. In other instances, the angle β of alignment horn 910 may be greater than or less than the angle β of tunneling member 920.

According to an exemplary embodiment, tunneling member 920 is formed from a medical grade metal rod, such as a series 300 stainless steel rod having a diameter in a range from approximately 0.1 inch (2.5 mm) to approximately 0.14 inch (3.5 mm), for example, approximately 0.122 inch (3 mm), and a length in a range from five inches (12.7 cm) to approximately eleven inches (28 cm), for example, approximately eight inches (20 cm); and handle 950 and alignment horn 910 are each formed from a relatively hard medical grade polymer, or a combination of medical grade metal and polymer, wherein horn 910 may extend over a length in a range from approximately five inches (12.7 cm) to approximately eleven inches (28 cm). In some alternate embodiments, tunneling member 920 may also be formed from a relatively hard medical grade polymer. Alignment horn 910, having the relatively straight extent (first end 911 or proximal/first segment) coplanar with, and parallel to the relatively straight extent of proximal segment 921 of tunneling member 920, provides an external reference for an operator who advances blunt tip 902 of tunneling member 920 within a body of a patient to form a sub-sternal tunnel with tool 900, as is described below in conjunction with FIG. 4A. The pre-formed bend of the distal segment 922 of tunneling member 920, which biases blunt tip 902 toward alignment horn 910, can cause tip 902 to 'ride' adjacent an underside of sternum 13 during sub-sternal tunneling; whereas, the pre-formed bend of alignment horn second end 912, in conjunction with blunt tip 901, make tool 900 suitable for forming, with alignment horn 910, a subcutaneous tunnel that curves around the patient's ribcage, as described below in conjunction with FIG. 4B. In other embodiments, alignment horn 910 may be relatively straight for the entire length form handle 950 to blunt tip 901.

Figure 3C:
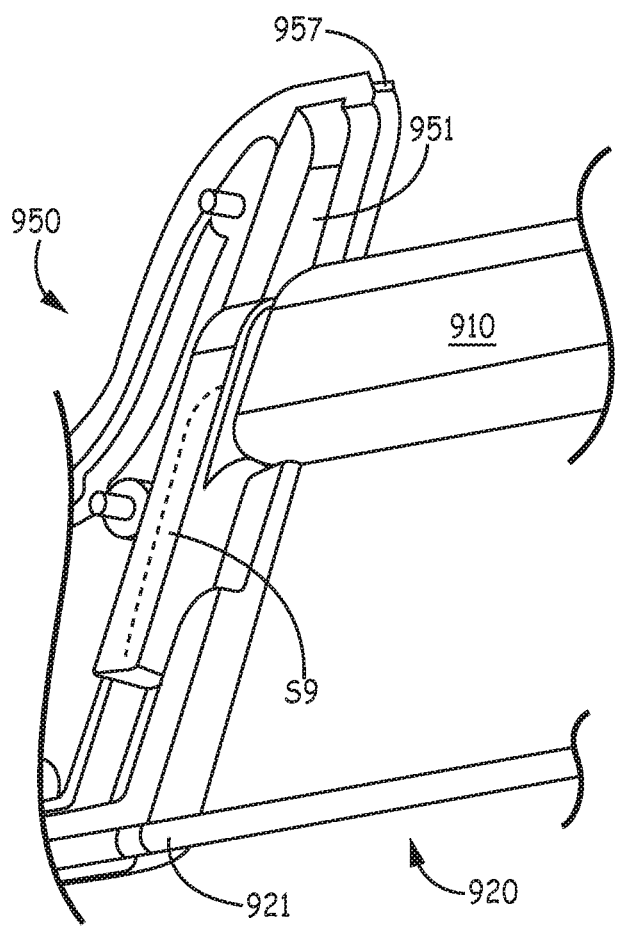

With further reference to FIG. 3A in conjunction with FIG. 3B, which is a cross-section view through section line B-B of FIG. 3A, according to some embodiments, alignment horn 910 may include an open channel 917 that extends from first end 911 to blunt tip 901 (represented by a dashed line in FIG. 3A), an entirety of which is directed away from tunneling member 920. Channel 917 may further extend into handle 950, as indicated by the dashed lines in FIG. 3A, and as designated with reference numeral 957 in FIG. 3C. FIG. 3B illustrates channel 917 having a width W and a depth D, for example, each being approximately the same or slightly larger than an outer diameter of a body of lead 16, to accommodate lead 16 being inserted therein. Alternate configurations of open channel 917 are not outside the scope of the instant application, for example, like those described for an open channel 36 of a shaft 34 used for tunneling in a co-pending and commonly assigned United States Patent Application having the pre-grant publication number 2015/0133952, the description of which are hereby incorporated by reference in its entirety. According to the illustrated embodiment, after employing horn 910 to form the aforementioned subcutaneous tunnel, the operator may advance a proximal portion of a medical electrical lead along open channel 917, for example, proximal portion 16-p of lead 16, to position the proximal portion within the subcutaneous tunnel, as described in greater detail below.

FIG. 3A further illustrates handle 950 of multi-purpose tool 900 including an optional lever 952, which is part of an optional lock-and-release mechanism that may form a junction between handle 950 and proximal segment 921 of tunneling member 920. According to embodiments that include the mechanism, lever 952, when lifted, or rotated, per arrow R, allows an operator to detach handle 950 from tunneling member 920, for example, prior to using alignment horn 910 to create the aforementioned subcutaneous tunnel. An enlarged detail view of the optional mechanism, which is enclosed within a shell of handle 950, is shown in FIG. 3A, wherein a block 955 is coupled to lever 952 via a dowel 956, and defines a portion 905 of a channel that extends within handle 950, and through which tunneling member proximal segment 921 extends. Channel portion 905, when offset from, or misaligned with, a remainder of the channel, locks tunneling member 920 with respect to handle 950, but, when lever 952 is rotated per arrow R, block 955 is moved to align channel portion 905 and thereby release tunneling member 920. Lever 952 may be formed from polycarbonate, and block 955 from stainless steel, PEI Ultem™ or PEEK. Although a specific lock and release mechanism is illustrated in FIG. 3A for exemplary purposes, other lock and release mechanisms may be used in handle 950, including some of those described elsewhere herein.

FIG. 3C is an enlarged detail view inside a yoke of handle 950 that illustrates another optional mechanism of multi-purpose tool 900, wherein the mechanism is an adjustment mechanism that allows an operator to move alignment horn 910 into a plurality of positions relative to tunneling member 920, while maintaining the parallel orientation therebetween. For example, the operator may move horn 910 from the position shown in FIG. 3A to others, per arrow A of FIG. 3A, which are closer to tunneling member 920, so that tool 900 can accommodate various sizes of patients, as described in greater detail below. FIG. 3C illustrates the adjustment mechanism being formed by a shank S9 of alignment horn 910 that is mounted in sliding engagement within a slot 951 of the handle yoke. In some embodiments, a flat, or leaf spring member (shown with dashed lines) may be mounted to a face of shank S9, and interface with a confronting face of slot 951 to hold alignment horn 910 in place by preventing horn 910 from freely sliding within slot 971, while allowing the operator to forcibly slide horn 910 to various positions. Although an example adjustment mechanism is illustrated in FIG. 3C for exemplary purposes, other adjustment mechanisms may be used in handle 950, including some of those described elsewhere herein.

Figure 4A:
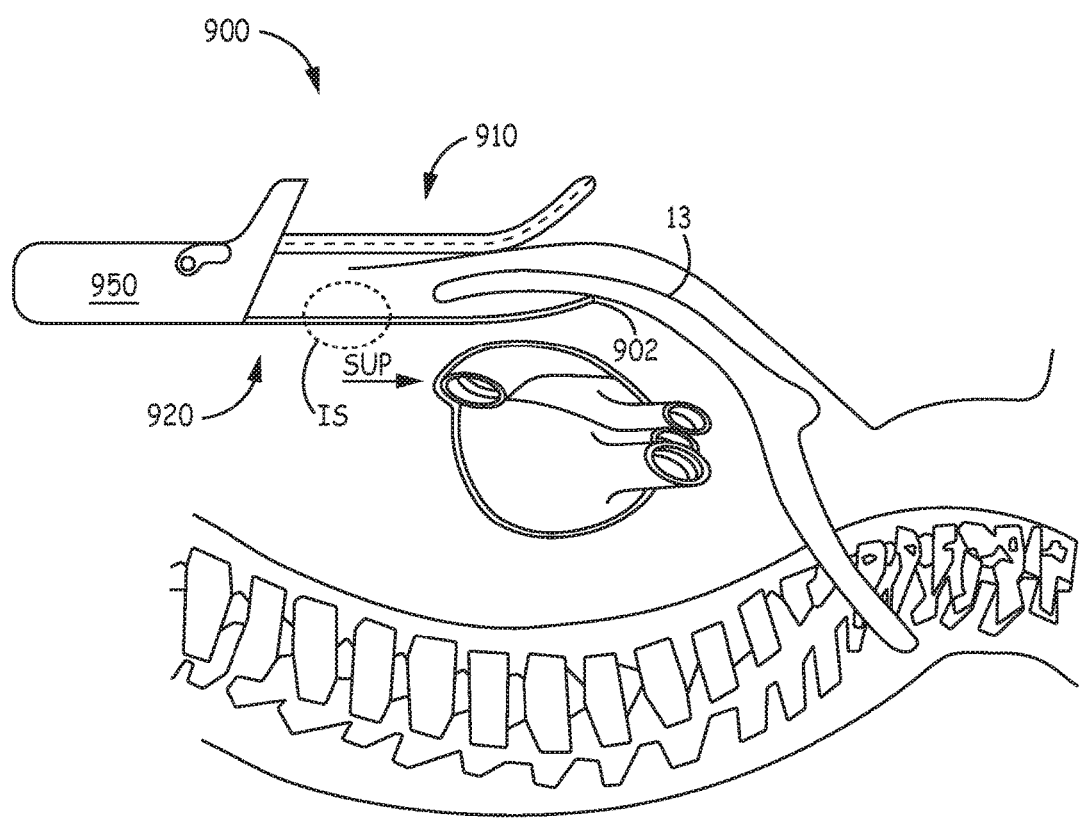
FIG. 4A-C are schematics outlining methods for using an example multi-purpose tool to implant a medical electrical lead in a patient.
Figure 4B:
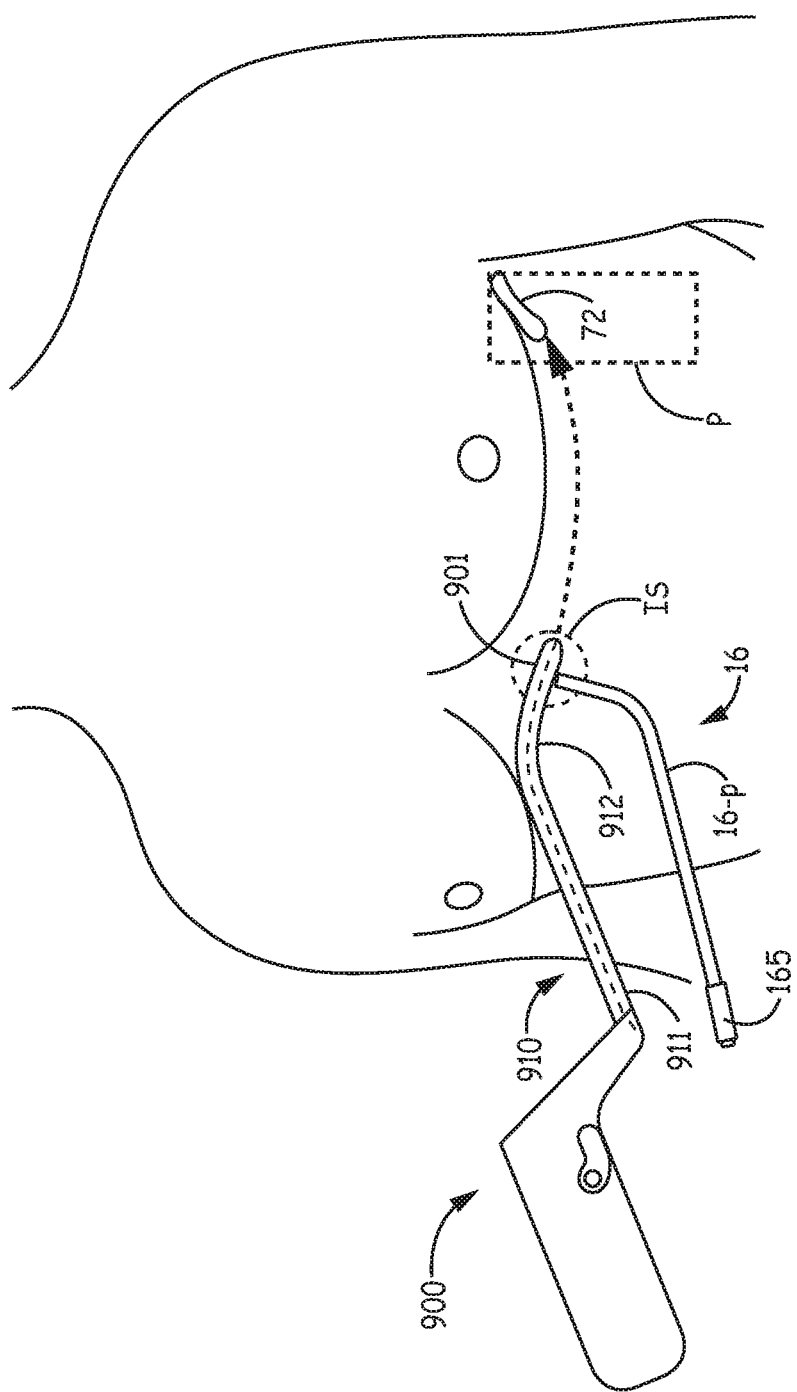
Figure 4C:
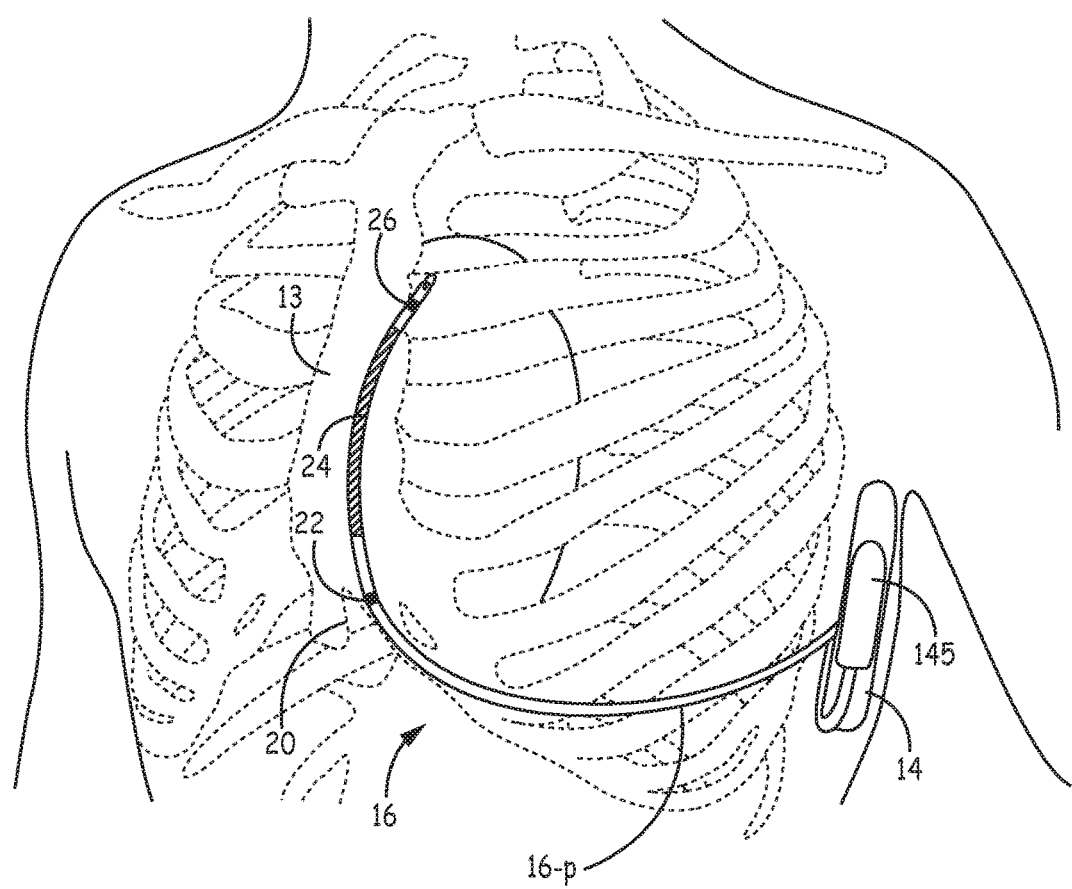

FIG. 4A-C are schematics outlining methods for using multi-purpose tool 900 or other similar multi-purpose tool. FIG. 4A illustrates tunneling member 920 of tool 900 having been inserted through an incision site IS of a patient and then advanced in a superior direction, per arrow SUP, beneath the patient's sternum 13, wherein alignment horn 910 of tool 900, as an external reference, guides the superior and sub-sternal advancement of tunneling member blunt tip 902. As was mentioned above, the pre-formed bend of tunneling member 920 biases blunt tip 902 toward horn 910 so that tip 902 rides adjacent to the underside of sternum 13 during the sub-sternal tunneling. Once the operator advances blunt tip 902 enough to create a sub-sternal tunnel of sufficient length, for example, being limited by the aforementioned length of tunneling member 920, and/or being stopped by a leading edge of handle 950, from which tunneling member 920 and horn 910 extend, an introducer sheath (not shown) may be advanced over tunneling member 920, for example, after detaching handle 950 therefrom. (Alternately, the introducer sheath may be positioned around tunneling member 920 prior to forming the sub-sternal tunnel therewith.) Then, the operator may remove tunneling member 920 from the sub-sternal tunnel and deliver a distal portion of a medical electrical lead, for example, the distal portion of lead 16 described above in conjunction with FIG. 1A, through a lumen of the introducer sheath to position the distal portion within the sub-sternal tunnel, for example, as shown in FIG. 4C. According to some methods, after the distal portion of lead 16 is positioned, a proximal portion 16-$p$ of lead 16 extends out from incision site IS, as illustrated in FIG. 4B. FIG. 4B further illustrates multi-purpose tool 900 being positioned for inserting blunt tip 901 of alignment horn 910 through incision site IS, after detaching handle 950 from tunneling member 920, according to some methods. The dotted-line arrow of FIG. 4B designates a path along which horn 910 may be advanced subcutaneously around the patient's ribcage to create the subcutaneous tunnel from incision site IS to a subcutaneous pocket P of the patient. Subcutaneous pocket P, for example, having been formed by blunt dissection through an incision 72, lies superficial to the patient's ribcage, and is sized to hold pulse generator 14, for example, as shown in FIG. 4C. As was mentioned above, the pre-formed bend of horn 910 can help the operator direct blunt tip 901 around the curvature of ribcage and toward the subcutaneous pocket P.

With further reference to FIG. 4B and according to some methods, when alignment horn 910 of tool 900 includes the open channel 917 described above in conjunction with FIGS. 3A-B, proximal portion 16-$p$ of lead 16 is advanced within channel 917 of the advanced horn 910 for positioning within the subcutaneous tunnel formed by horn 910, so that a connector terminal 165 of lead 16 ends up in subcutaneous pocket P for coupling to pulse generator 14 via connector module 145, as shown in FIG. 4C. According to some embodiments, horn 910 may be detachable from handle 950 by separation from shank S9 (FIG. 3C), so that, according to some alternate methods, the operator may secure lead connector terminal 165 within open channel 917, in proximity to first end 911 of detached horn 910, after advancing horn 910 to form the subcutaneous tunnel, and so that second end 912 of horn extends out from pocket P, and then apply a pull force to second end 912 to pull lead proximal portion 16-$p$ through subcutaneous tunnel.

According to some alternate methods, after alignment horn 910 forms the subcutaneous tunnel, horn 910 may be withdrawn therefrom before positioning lead proximal portion 16-$p$ within the tunnel, for example, via an introducer sheath, in a similar manner to that described above for positioning the distal portion of lead 16 in the sub-sternal tunnel.

FIG. 5A is a plan view of a multi-purpose tool 500, according to some alternate embodiments. FIG. 5A illustrates tool 500 including a handle 550, an elongate tunneling member 520, which is detachably coupled to handle 550, and an alignment horn 510, which has a first end 511 coupled to handle 550, and which extends, alongside and coplanar with tunneling member 520, from first end 511 to a second end 512 of horn 510, being relatively straight therebetween, and parallel to a relatively straight proximal segment 521 of tunneling member 520. FIG. 5A further illustrates tunneling member 520 including a blunt tip 502, wherein a distal segment 522 of tunneling member 520 extends along a single pre-formed bend from proximal segment 521 to blunt tip 502, such that blunt tip 502 is directed toward alignment horn 510. According to the illustrated embodiment, tunneling member proximal segment 521 and distal segment 522 are coplanar and enclose angle $\beta$. In one example, the angle $\beta$ may be between approximately 150 degrees and approximately 170 degrees. However, angles greater than 170 degrees (but less than 180 degrees) and angles less than 150 degrees (but greater than 90 degrees) may also be utilized without departing from the scope of this disclosure. Similarly, second end 512 of alignment horn 520 extends along a single pre-formed bend and is terminated by a blunt tip 501; and second end 512 of alignment horn 510 is coplanar with the relatively straight remainder of horn 510, wherein an angle enclosed by second end 512 and the remainder may be similar to angle $\beta$ of tunneling member 520. In other instances, the angle of alignment horn 510 may be different than the angle $\beta$ of tunneling member 520. In other embodiments, alignment horn 510 may be relatively straight for the entire length form handle 550 to blunt tip 501.

According to some exemplary embodiments, tunneling member 520 is formed from a medical grade metal rod, such as a series 300 stainless steel rod having a diameter in a range from approximately 0.1 inch (2.5 mm) to approximately 0.14 inch (3.5 mm), for example, approximately 0.122 inch (3 mm); and the coupling between tunneling member 520 and handle 550, which allows for the detachment of handle 550 from tunneling member 520, may be formed by a threaded interface therebetween. Handle 550 and alignment horn 510 may each formed from a relatively hard medical grade polymer. In some alternate embodiments, tunneling member 520 may also be formed from a relatively hard medical grade polymer.

With reference back to FIG. 4A, multi-purpose tool 500 may be used in a similar fashion to that described above for tool 900 in order to create a sub-sternal tunnel by inserting blunt tip 502 of tunneling member 520 through incision site IS and then advancing tunneling member 520 in the superior direction, per arrow SUP, beneath the patient's sternum 13, being guided by the external reference of alignment horn 510. In FIG. 5A handle 550 is shown extending at an angle $\varphi$ with respect to tunneling member proximal segment 521, for example, to provide some clearance for an operator's hand while handling and manipulating tool 500 to create the substernal tunnel. Also like tool 900, according to some methods, after forming the sub-sternal tunnel with tool 500, the operator may detach handle 550 from tunneling member 520 to position an introducer sheath within the sub-sternal tunnel, and then position the distal portion of lead 16, through the sheath, within the sub-sternal tunnel, as described above. Then the operator can use tool 500 to create, with alignment horn 510, a subcutaneous tunnel from incision site IS to subcutaneous pocket P, for example, along the dashed line arrow shown in FIG. 5B.

FIG. 5A further illustrates handle 550 including a pivot joint 551 that couples first end 511 of alignment horn 510 to handle 550 so that handle 550 may be swiveled relative to alignment horn 510, per arrow S, for example, to the orientation shown with dashed lines, after tunneling member 520 is detached therefrom. FIG. 5B is a schematic showing tool 500 re-oriented (e.g., flipped 180 degrees, around a longitudinal axis of horn 510, from the orientation of FIG. 5A, which corresponds to sub-sternal tunneling per FIG. 4A) for creating the above described subcutaneous tunnel, from incision site IS to subcutaneous pocket P, after detaching tunneling member 520 from handle 550, and swiveling handle 550, relative to alignment horn 510. Dashed lines in FIG. 5A designate an optional open channel extending along horn 510 from first end 511 to blunt tip 501, similar to that of horn 910 of tool 900, for example, being configured to receive insertion of lead proximal portion 16-$p$ therein, to position proximal portion 16-$p$ within the subcutaneous tunnel.

FIGS. 6A-B are plan views of a multi-purpose tool 600, according to yet further embodiments. FIGS. 6A-B illustrate tool 600 including a handle 650, an elongate tunneling member 620, which has a proximal segment 621 joined to handle 650, and an alignment horn 610, which has a first end 611 coupled to handle 650, and which extends, alongside and coplanar with tunneling member 620, from first end 611 to a second end 612 of horn 610, being relatively straight therebetween, and parallel to tunneling member proximal segment 621. FIGS. 6A-B further illustrate tunneling member 620 including a blunt tip 602, wherein a distal segment 622 of tunneling member 620 extends along a single pre-formed bend from proximal segment 621 to blunt tip 602, such that tunneling member proximal segment 621 and distal segment 622 are coplanar and enclose an angle β, for example, which may be between approximately 150 degrees and approximately 170 degrees. However, angles greater than 170 degrees (but less than 180 degrees) and angles less than 150 degrees (but greater than 90 degrees) may also be utilized without departing from the scope of this disclosure. Tunneling member 620, for example, formed from a medical grade metal rod, may have a diameter and length similar to that of tunneling member 920 of tool 900; and handle 650 and alignment horn 610 may each formed from a relatively hard medical grade polymer, or a combination of medical grade metal and polymer. In some alternate embodiments, tunneling member 920 may also be formed from a relatively hard medical grade polymer. With further reference to FIGS. 6A-B, handle 650 of tool 600 preferably includes a looped gripping portion to accommodate various operator hand sizes, with finger recesses 653 formed therein. Handle 650 may further include an adjustment mechanism like that described above, in conjunction with FIGS. 3A and 3C, for handle 950 of tool 900, which allows an operator to move alignment horn 610 into a plurality of positions relative to tunneling member 620, according to different sizes of patients, while maintaining the parallel orientation therebetween. Although an example adjustment mechanism is illustrated in FIGS. 6A and 6B for exemplary purposes, other adjustment mechanisms may be used in handle 650, including some of those described elsewhere herein.

According to the illustrated embodiment, handle 650 further includes a lock-and-release mechanism, for example, like that described above for handle 950 of tool 900 (FIG. 3A), which forms a junction between handle 650 and proximal segment 621 of tunneling member 620, and which includes lever 952. When lever 952 of the lock-and-release mechanism is lifted or rotated, per arrow R, handle 650 can be detached from tunneling member 620, or tunneling member 620 rotated relative to handle 650, around a longitudinal axis 6 thereof (defined by tunneling member proximal segment 621), for example, from a first position (FIG. 6A) to a second position (FIG. 6B). Although a specific lock and release mechanism is illustrated in FIGS. 6A and 6B for exemplary purposes, other lock and release mechanisms may be used in handle 650, including some of those described elsewhere herein.

Figure 7A:
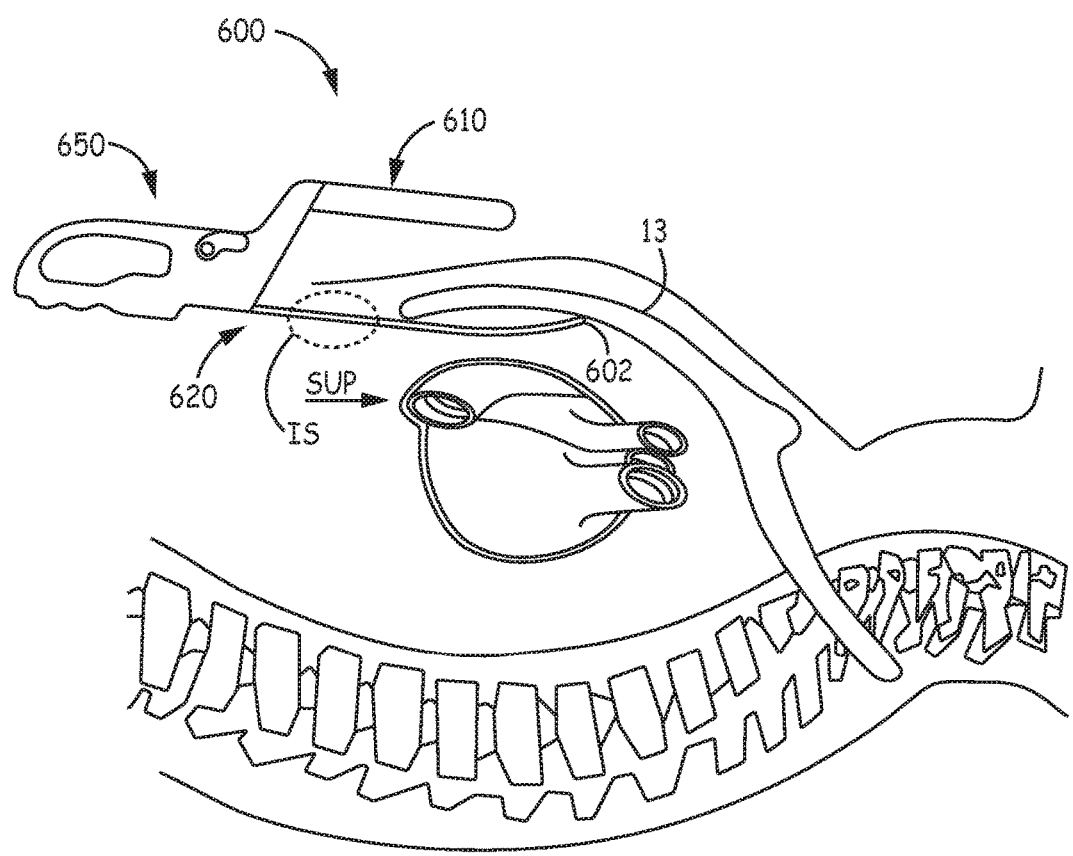
FIG. 7A-D are schematics outlining another example method for using an example multi-purpose tool to implant a medical electrical lead.
Figure 7B:
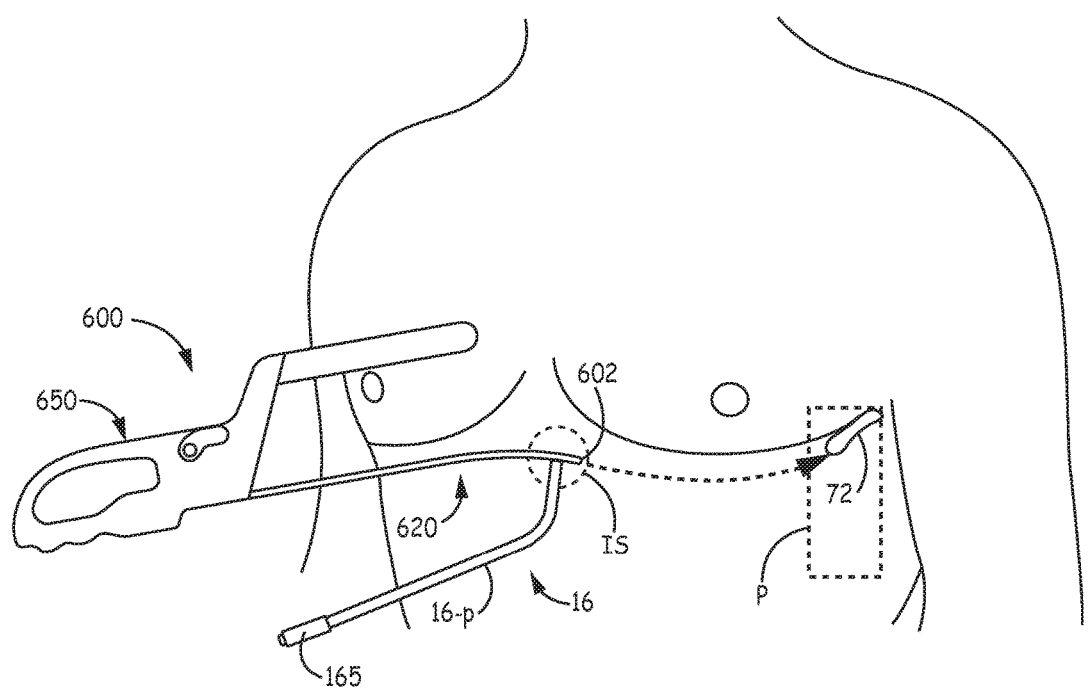

FIG. 6A shows tunneling member 620 in the first position, at which distal segment 622 extends toward alignment horn 610, so that tool 600 may be used by an operator to create the above-described sub-sternal tunnel. Alignment horn 610, as an external reference, guides the operator in the superior and sub-sternal advancement of tunneling member blunt tip 602 to create the sub-sternal tunnel, and the pre-formed bend of tunneling member 620 causes blunt tip 602 to ride adjacent the underside of sternum 13 during the superior advancement thereof when tunneling, for example, as illustrated in the schematic of FIG. 7A. FIG. 6B shows tunneling member 620 having been rotated 180 degrees from the first position to the second position, at which distal segment 622 extends directly away from alignment horn 910, so that tool 600 may be used by the operator to create the above-described subcutaneous tunnel, with the pre-formed bend of tunneling member 620 oriented to guide blunt tip 602 around the curvature of the patient's ribcage and toward the subcutaneous pocket P, for example, as illustrated by the schematic of FIG. 7B.

According to some methods, once the sub-sternal tunnel is created, the operator may detach handle 650 from tunneling member 620 to pass an introducer sheath over tunneling member 620 and into the sub-sternal tunnel, so that, when tunneling member 620 is withdrawn from the tunnel, lead distal portion can be advanced through the introducer sheath for positioning in the sub-sternal tunnel. FIG. 7B illustrates lead proximal portion 16-$p$ extending out from incision site IS, after the lead distal portion has been positioned in the sub-sternal tunnel, and tunneling member 620 of tool 600 having been rotated to the second position, such that distal segment 622 extends directly away from alignment horn 910. FIG. 7B further illustrates blunt tip 602 of tunneling member 620 directed for insertion into incision site IS to create the subcutaneous tunnel, for example, along the dashed line arrow.

Figure 7C:
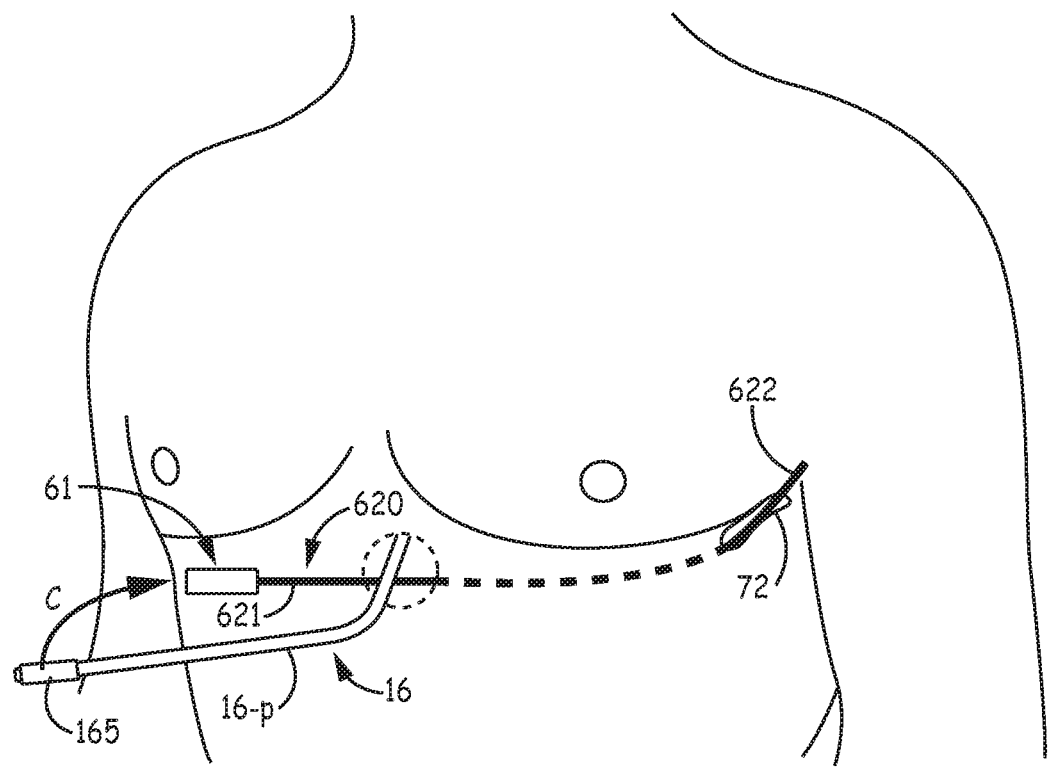
Figure 7D:
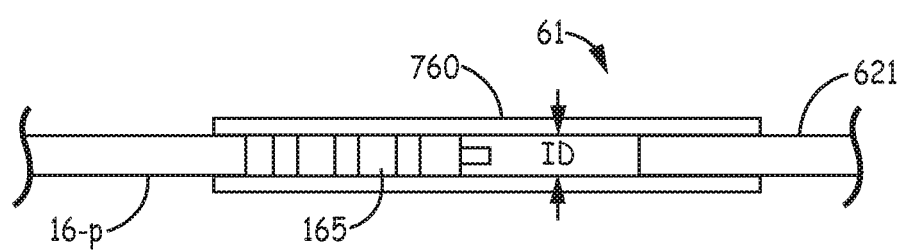

Once the subcutaneous tunnel from incision site IS to pocket P is formed, the operator may detach handle 650 from proximal segment 621 of tunneling member 620, as shown in FIG. 7C. FIG. 7C illustrates distal segment 622 of tunneling member 620 protruding out through incision 72, which corresponds to subcutaneous pocket P, and a proximal end 61 of tunneling member proximal segment 621 protruding from incision site IS and being configured for attachment of lead connector terminal 165 thereto, for example, by insertion per arrow C. According to some methods, the operator may configure tunneling member proximal end 61 by securing an elastic tube 760 to proximal segment 621 of tunneling member 620 after detaching handle 650 therefrom, for example, as shown in FIG. 7D. FIG. 7D is a longitudinal cross-section through the secured tube 760 that forms proximal end 61, wherein lead connector terminal 165 is shown inserted therein for attachment to tunneling member 620. According to the illustrated embodiment, tube 760 has an inner diameter ID that forms an interference fit around tunneling member proximal segment 621 and lead connector terminal 165, and tube 760 may be formed from medical grade silicone rubber, for example, by an extrusion process. According to an exemplary embodiment, tube inner diameter ID is approximately 0.094 inch (2.4 mm) and a length L of tube 760 is may be as short as approximately one inch (2.5 cm) and as long as up to approximately 10 inches (25 cm). Once lead connector terminal 165 is attached to tunneling member 620, the operator may grasp distal segment 622 of tunneling member 620 and apply a pull force thereto to withdraw an entirety of tunneling member 620 from the subcutaneous tunnel, through incision 72, which pulls lead proximal portion 16-p into the tunnel so that connector terminal 165 extends into pocket P. Then, after withdrawing connector terminal 165 from tubing 760, the operator can couple connector terminal 165 to pulse generator 14, as described above and shown in FIG. 4C.

According to some additional embodiments, tunneling member 620 of tool 600 includes an open channel, extending along an entirety of the length, or extending just along proximal segment 621. In these embodiments, the channel of tunneling member 620 may have a configuration similar to any of those described above for channel 917 of alignment horn 910 in tool 900 (FIG. 3B), for example, to accommodate the attachment of lead proximal portion 16-p to tunneling member 620, as an alternative to the above-described proximal end 61. According to some alternate methods, after the operator creates the sub-sternal tunnel with tunneling member 620 of tool 600, which does not have an open channel, the operator may exchange tunneling member 620 for another tunneling member that has an open channel (like any embodiment of channel 917 described above) to create the subcutaneous tunnel.

In the foregoing detailed description, various tool features have been described with reference to specific embodiments. However, it may be appreciated that various modifications and changes can be made without departing from the scope of the invention as set forth in the appended claims. For example, one or more features of a particular exemplary embodiment may be employed by other exemplary embodiments in the same or alternative forms. Additionally, in alternative embodiments of the methods described in FIGS. 4, 5 and 7, the multi-purpose implant tool may be used to form the subcutaneous tunnel first (e.g., from either incision IS to pocket 72 or from pocket 72 to incision IS) and place the proximal portion of the lead, e.g., proximal portion 16-p of lead 16, within the subcutaneous tunnel and then be used to form the substernal tunnel and place the distal portion of the lead within the substernal space.

The invention claimed is:

1. A multi-purpose tunneling tool comprising:
an elongate tunneling member including a relatively straight proximal segment, a distal segment, and a blunt tip, the proximal segment defining a longitudinal axis of the tunneling member, the distal segment extending along a single pre-formed bend from the proximal segment to the blunt tip, the distal segment being co-planar with the proximal segment, and the segments enclosing an angle of between approximately 150 degrees and approximately 170 degrees;
a handle including a lock-and-release mechanism that forms a junction between the handle and the proximal segment of the tunneling member; and
an alignment horn extending from a first end thereof to a second end thereof, alongside and coplanar with the tunneling member, the horn being relatively straight between the first and second ends thereof and substantially parallel to the tunneling member proximal segment, the first end of the alignment horn being coupled to the handle; and
wherein the lock-and-release mechanism of the handle is configured to allow detachment of the handle from the tunneling member, and to allow rotation of the tunneling member 180 degrees about the longitudinal axis thereof, relative to the handle, from a first position to a second position, the tunneling member distal segment extending directly toward the alignment horn in the first position, and the tunneling member distal segment extending directly away from the alignment horn in the second position.

2. The tool of claim 1, wherein the alignment horn includes a blunt tip terminating the second end thereof, the second end of the alignment horn extending along a single pre-formed bend, such that the blunt tip of the horn is directed away from the tunneling member, the second end being co-planar with a relatively straight remainder of the horn, and the second end and remainder enclosing an angle of between approximately 150 degrees and approximately 170 degrees.

3. The tool of claim 2, wherein the alignment horn further includes an open channel extending from the first end thereof to the blunt tip thereof, an entirety of the open channel being directed away from the tunneling member.

4. The tool of claim 1, wherein the handle further comprises a pivot joint coupling the first end of the alignment horn thereto.

5. The tool of claim 1, wherein the handle includes an adjustment mechanism configured to move the alignment horn into a plurality of positions relative to the tunneling member, without changing the parallel extent of the horn and the proximal segment of the tunneling member.

6. The tool of claim 1, wherein the tunneling member further includes an open channel extending along a length thereof.

7. The tool of claim 1, wherein the alignment horn further includes an open channel extending from the first end thereof to the blunt tip thereof, an entirety of the open channel being directed away from the tunneling member.

8. A multi-purpose tunneling tool comprising:
an elongate tunneling member including a relatively straight proximal segment, a distal segment, and a blunt tip, the proximal segment defining a longitudinal axis of the tunneling member, the distal segment extending along a single pre-formed bend from the proximal segment to the blunt tip, the distal segment being co-planar with the proximal segment, and the segments enclosing an angle of between approximately 150 degrees and approximately 170 degrees;
a handle joined to the proximal segment of the tunneling member; and
an alignment horn including a first end, a second end, and a blunt tip terminating the second end, the horn extending from the first end to the second end alongside and coplanar with the tunneling member, and the horn being relatively straight between the first and second ends thereof and parallel to the proximal segment of the tunneling member, the first end of the alignment horn being coupled to the handle, the second end of the alignment horn extending along a single pre-formed bend, such that the blunt tip of the horn is directed away from the tunneling member, the second end being co-planar with a relatively straight remainder of the horn, and the second end and remainder enclosing an angle of between 150 degrees and 170 degrees, wherein the alignment horn is configurable into a plurality of positions relative to the tunneling member without changing the parallel extent of the horn and the proximal segment of the tunneling member.

9. The tool of claim 8, wherein the alignment horn further includes an open channel extending from the first end thereof to the blunt tip thereof, an entirety of the open channel being directed away from the tunneling member.

10. The tool of claim 8, wherein the alignment horn is detachable from the handle.

11. The tool of claim 8, wherein the handle includes an adjustment mechanism configured to move the alignment horn into a plurality of positions relative to the tunneling member, without changing the parallel extent of the horn and the proximal segment of the tunneling member.

12. The tool of claim 8, further comprising a lock-and-release mechanism that forms a junction between the handle and the proximal segment of the tunneling member, wherein the tunneling member is detachable from the handle via the lock-and-release mechanism.

13. A method for employing a tunneling tool, the method comprising:

creating a sub-sternal tunnel in a patient by advancing an elongate tunneling member of the tool beneath a sternum of the patient, after having inserted a blunt tip of the tunneling member through an incision site of the patient, the advancing being guided by an alignment horn of the tool, the tunneling member further including a relatively straight proximal segment, and a distal segment extending along a single pre-formed bend from the proximal segment to the blunt tip, the distal segment being co-planar with the proximal segment, and the alignment horn extending from a first end thereof to a second end thereof, alongside and coplanar with the tunneling member, the horn being relatively straight between the first and second ends thereof and parallel to the proximal segment of the tunneling member;

removing the tunneling member of the tool from the sub-sternal tunnel;

positioning a distal portion of a medical electrical lead within the sub-sternal tunnel, after removing the tunneling member;

creating a subcutaneous tunnel superficial to a rib cage of the patient, after creating the sub-sternal tunnel and removing the tunneling member of the tool therefrom, by inserting a blunt tip of the alignment horn of the tool through the incision site and then advancing the alignment horn subcutaneously around the rib cage to a subcutaneous pocket of the patient, the blunt tip of the alignment horn terminating the second end of the horn, and the second end of the horn extending along a single pre-formed bend, such that the blunt tip of the horn is directed away from the tunneling member, the second end being co-planar with a relatively straight remainder of the horn; and positioning a proximal portion of the medical electrical lead within the subcutaneous tunnel, so that a connector terminal of the lead extends into the subcutaneous pocket.

14. The method of claim 13, wherein positioning the proximal portion of the lead within the subcutaneous tunnel comprises advancing the proximal portion along an open channel of the advanced alignment horn of the tool, the open channel extending from the first end of the alignment horn to the blunt tip of the horn.

15. A method for employing a tunneling tool to create a subcutaneous tunnel with in a patient, and to position a proximal portion of a medical electrical lead within the subcutaneous tunnel, after creating a sub-sternal tunnel in the patient with the tunneling tool, the method comprising:

rotating an elongate tunneling member of the tool 180 degrees relative to a handle of the tool so that a blunt tip of the tunneling member is directed away from an alignment horn of the tool, the tunneling member further including a relatively straight proximal segment joined to the handle and a distal segment extending along a pre-formed bend from the proximal segment to the blunt tip, the distal segment being coplanar with the with the proximal segment, and the alignment horn extending from a first end thereof to a second end thereof, alongside and coplanar with the proximal segment of the tunneling member, the horn being relatively straight between the first and second ends thereof and parallel to the proximal segment of the tunneling member;

advancing the rotated tunneling member subcutaneously around a rib cage of the patient until the blunt tip reaches a subcutaneous pocket of the patient;

detaching the handle from the proximal segment of the advanced tunneling member, the handle including a lock-and-release mechanism joining the proximal segment of the tunneling member thereto;

attaching a connector terminal of the proximal portion of the medical electrical lead to the proximal segment of the advanced tunneling member, after detaching the handle; and applying a pull force to the distal segment of the advanced tunneling member, after attaching the connector terminal of the lead proximal portion to the proximal segment thereof, to bring the connector terminal through the subcutaneous tunnel and into the subcutaneous pocket.

* * * * *